(12) United States Patent
Hernandez et al.

(10) Patent No.: US 11,497,486 B2
(45) Date of Patent: Nov. 15, 2022

(54) ENDOSCOPIC NEEDLE CARRIER

(71) Applicants: IRCAD, INSTITUT DE RECHERCHE CONTRE LES CANCERS DE L'APPAREIL DIGESTIF, Strasbourg (FR); INSTITUT HOSPITALO-UNIVERSITAIRE DE CHIRURGIE MINI-INVASIVE GUIDEE PAR L'IMAGE, Strasbourg (FR)

(72) Inventors: Juan Hernandez, Strasbourg (FR); Andras Legner, Strasbourg (FR)

(73) Assignees: IRCAD, INSTITUT DE RECHERCHE CONTRE, LES CANCERS DE L'APPAREIL DIGESTIF, Strasbourg (FR); INSTITUT HOSPITALO-UNIVERSITAIRE DE CHIRURGIE MINI-INVASIVE GUIDEE PAR L'IMAGE, Strasbourg (FR)

( * ) Notice: Subject to any disclaimer, the term of this patent is extended or adjusted under 35 U.S.C. 154(b) by 610 days.

(21) Appl. No.: 16/331,833

(22) PCT Filed: Sep. 1, 2017

(86) PCT No.: PCT/FR2017/052318
§ 371 (c)(1),
(2) Date: Mar. 8, 2019

(87) PCT Pub. No.: WO2018/046822
PCT Pub. Date: Mar. 15, 2018

(65) Prior Publication Data
US 2019/0374217 A1     Dec. 12, 2019

(30) Foreign Application Priority Data

Sep. 9, 2016   (FR) .................................. 16/58445

(51) Int. Cl.
*A61B 17/04*     (2006.01)
*A61B 17/062*    (2006.01)
(Continued)

(52) U.S. Cl.
CPC ........ *A61B 17/0469* (2013.01); *A61B 17/062* (2013.01); *A61B 2017/00398* (2013.01);
(Continued)

(58) Field of Classification Search
CPC ... A61B 17/0469; A61B 17/062; A61B 17/28; A61B 17/29; A61B 2017/00398;
(Continued)

(56) References Cited

U.S. PATENT DOCUMENTS 3,140,715 A * 7/1964 Whitton, Jr. ........... A61B 17/30
606/210
5,300,082 A   4/1994 Sharpe et al.
(Continued)

FOREIGN PATENT DOCUMENTS

DE       19750008 C1   6/1999
WO    WO-2011/055684 A1   5/2011

*Primary Examiner* — Erich G Herbermann
(74) *Attorney, Agent, or Firm* — Harness Dickey & Pierce PLC

(57) ABSTRACT

An endoscopic needle holder for handling curved needles includes an articulated assembly including a first gripping jaw forming one piece with a duct and a second gripping jaw actuated by the movable core in transverse displacement; the jaws are made of coaxial cylindrical parts with the mobile core; the first jaw has a plurality of longitudinally extending peripheral teeth; the second jaw consists of a cylindrical part with a plurality of peripheral teeth; and the second jaw is movable with respect to the first jaw by a longitudinal linear
(Continued)

displacement between a rest position, where the jaws are spaced to delimit, between the ends of the teeth, an interval at least equal to the section of a needle and a close position where they keep the needle curved.

27 Claims, 14 Drawing Sheets

(51) Int. Cl.
  *A61B 17/00* (2006.01)
  *A61B 17/29* (2006.01)
(52) U.S. Cl.
  CPC .............. *A61B 2017/00862* (2013.01); *A61B 2017/2926* (2013.01)
(58) Field of Classification Search
  CPC .. A61B 2017/00862; A61B 2017/2926; A61B 2017/2944; A61B 2017/1125; A61B 17/04; A61B 17/0482; A61B 17/06061; A61B 17/0485; A61B 2017/047
  See application file for complete search history.

(56) References Cited

U.S. PATENT DOCUMENTS

| | | | |
|---|---|---|---|
| 7,635,386 B1* | 12/2009 | Gammie | A61B 17/0482 623/2.11 |
| 8,480,689 B2 | 7/2013 | Spivey et al. | |
| 2005/0283139 A1 | 12/2005 | Iizuka et al. | |
| 2010/0280138 A1* | 11/2010 | Mofakhami | C04B 35/583 521/27 |
| 2011/0190794 A1 | 8/2011 | Dingler et al. | |
| 2011/0224718 A1* | 9/2011 | Torgerson | A61B 17/0625 606/207 |
| 2011/0270281 A1* | 11/2011 | Malkowski | A61B 17/062 606/147 |
| 2015/0164508 A1 | 6/2015 | Hernandez et al. | |
| 2015/0342608 A1 | 12/2015 | Hernandez | |
| 2019/0290260 A1* | 9/2019 | Caffes | A61B 17/0482 |

* cited by examiner

Fig. 17  Fig. 18  Fig. 19  Fig. 20
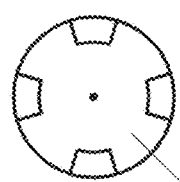
110
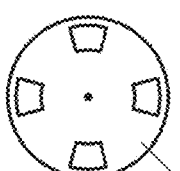
110
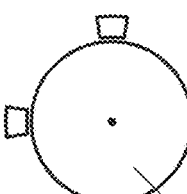
110
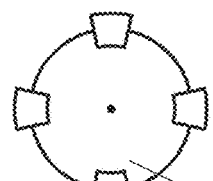
110
Fig. 21  Fig. 22  Fig. 23  Fig. 24  Fig. 25  Fig.26
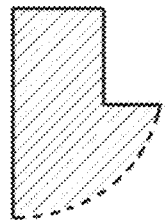
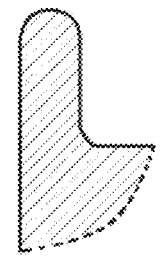
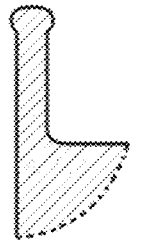
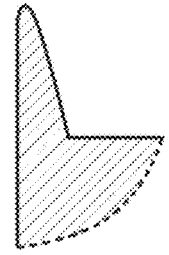
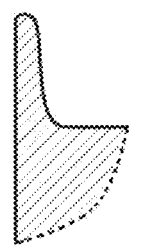
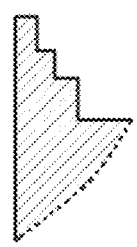
Fig. 27  Fig. 28  Fig. 29
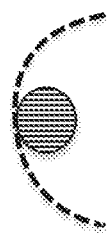

ENDOSCOPIC NEEDLE CARRIER

CROSS-REFERENCE TO RELATED APPLICATIONS

This application is a National Phase Entry of International Patent Application No. PCT/FR2017/052318, filed on Sep. 1, 2017, which claims priority to French Patent Application No. 16/58445, filed on Sep. 9, 2016, both of which are incorporated by reference herein.

TECHNICAL FIELD

This invention relates to the field of needle holders for grasping and suturing in minimally invasive endoscopic surgery or laparoscopy. Such needle holders usually consist of a forceps with two articulated jaws and placed at the end of a shaft. One of the jaws is in a fixed position, and the other is actuated by the handle of the endoscope with a gripping surface of the needle.

In laparoscopy, the forceps is used alone; in flexible endoscopy, it is introduced through a flexible endoscope. The invention more particularly relates to a needle holder for endoscopic manipulation of curved suture needles, applied to flexible endoscopy, laparoscopy and robotic versions. Handling such needles has difficulties even for an experienced surgeon because the curved needles tend to rotate inside the pair of jaws that hold the needle.

BACKGROUND

For example, we know of U.S. Pat. No. 5,257,999 that describes a laparoscopic needle holder made up of a stem and a set of jaws controlled at one end by an opening and closing mechanism. The gripping surfaces of the jaws are in-curved to adapt to a curved surgical needle. One jaw has a convex shape while the other jaw has a corresponding concave shave. The shape of the gripping surfaces of the incurved jaws automatically directs the curved surgical needle to a desired suture position. The shape of the set of jaws also makes it easy to release and grip the curved surgical needle again during the suturing process of a laparoscopic operation.

Also known is U.S. Pat. No. 8,480,689 describing a suture device for gripping a flexible needle to adopt an incurved rest state.

Also known is a solution described in U.S. Patent Publication No. 2011/190794 concerning a medical needle holder consisting of a handle disposed at the proximal end and a needle receiver disposed at the distal tip. The needle receiver has a first and a second gripping surface that face gripping surfaces each other and extend in a transverse direction to the longitudinal axis of the carrier. The gripping surfaces are movable relative to each other via the handle, in the direction of the longitudinal axis of the support.

U.S. Patent Publication No. 2011/270281 discloses another example of a needle holder having an elongated body portion with a proximal end and a distal tip. A rotating head is configured to be disposed at the distal end of the body portion and an actuating member configured to be arranged at the proximal end of the body portion. The actuator is in functional cooperation with a handle assembly to allow rotational movement of the rotating head. The rotating head further cooperates with a moving needle in relation to the rotating head.

With the solutions of the prior art, the surgeon has to angularly direct the jaws, generally articulated relative to a transverse pivot, in order to fit the needle between the two jaws, and then close these jaws on the needle. The initial step of directing the jaws, angularly and in depth, can be very delicate and sometimes requires several tens of minutes of trial and error, especially when the needle to be grasped is in an area of low endoscopic visibility or is inconveniently positioned. With the solutions of the prior art, the gripping of the needle is done with a precise radial direction, corresponding to the symmetry plane of the jaws and the orientation in this plane from the centre line to the open space between the two jaws. Even when the surgeon is able to position the jaws angularly and longitudinally with respect to the needle, he still has to control the radial movement to position the needle at the right level between the jaws. These procedures are particularly delicate in endoscopic surgery, where the needle is just hard to see and where the surgeon has little information on the progress of his trial and error. The solution proposed by U.S. Patent Publication Nos. 2011/90794 or 2011/270281 is also unsatisfactory because it allows only a very poor maintenance of the needle, which tends to disengage as soon as it exerts an effort to make it penetrate into tissue.

SUMMARY

In order to remedy these drawbacks, the invention, in its most general sense, relates to an endoscopic needle holder for handling curved needles comprising a remote actuating mechanism provided at one of the ends of the needle holder, and at the other end an articulated assembly comprising a first gripping jaw forming one piece with a duct and a second movable gripping jaw actuated by the mobile core in transverse displacement, characterized in that:
  said jaws are made up of coaxial cylindrical parts with said mobile core;
  said first jaw has a plurality of peripheral teeth extending longitudinally;
  said second jaw is made up of a cylindrical part that has a plurality of peripheral teeth angularly offset in relation to the teeth of the first jaw;
  said second jaw is mobile with respect to the first jaw by a longitudinal linear movement between a rest position, where the jaws are spaced to delimit, between the ends of the teeth, an interval at least equal to the section of a needle and a close position where they keep the needle curved.

The first jaw is fixed in transverse displacement but may nevertheless have a degree of freedom in rotation about the longitudinal axis with respect to the tube. It is constrained in transverse displacement with respect to the tube and constrained in rotation with respect to the second jaw (by means of a polygonal stem for example).

According to the embodiment, the teeth are fixed with respect to the jaw, or elastically retractable. According to a variant, said first jaw has a transverse frontal surface provided with a plurality of peripheral teeth extending perpendicularly to said front surface:
  said second jaw consists of a cylindrical piece having a transverse surface provided with a plurality of peripheral teeth;
  said jaws are movable by longitudinal linear movement between a rest position, where the jaws are spaced to delimit, between the ends of the teeth, an interval at least equal to the section of a needle and a close position where they keep the needle curved.

With the solution proposed by the invention, the gripping end has a circular geometry that no longer requires a particular radial orientation with respect to the position of the needle. Whatever the position of the needle in the transverse plane passing between the two jaws, it can be hooked by one or more teeth, and the approximation of the jaws can then grasp and hold it firmly. According to one variant, the teeth of the second jaw are angularly offset with respect to the teeth of the first jaw.

Preferably, said jaws have an alternation of peripheral teeth and peripheral grooves of shapes and positions that are complementary to the teeth of the opposite jaw. According to an advantageous variant, said teeth in the transverse plane have a polygonal cross section. According to a particular embodiment, each jaw has three teeth and three grooves for receiving the teeth of the complementary jaw. According to an advantageous variant, the outer surface of the teeth is semi-cylindrical.

According to different variants:
The enveloping surface of said teeth has a section that is identical to the section of said jaws. The outer surface thus extends the periphery of the corresponding jaw to have a peripheral surface devoid of asperities.
The enveloping surface of said teeth has a section which is smaller than the section of said jaws. In this case, the teeth are recessed from the perimeter of the corresponding jaw, which prevents the ends of the teeth from damaging the tissues in contact with the end of the endoscope.
The enveloping surface of said teeth has a section which is greater than the section of said jaws. In this case, the teeth protrude from the periphery of the corresponding jaw. This enables the attachment of the curved needle when it is close to the jaws.

According to a variant, said second jaw has a hemispherical end. It thus facilitates the introduction of the distal tip of the needle holder into hollow organs. According to different variants, the section of said teeth, in a radial plane:
has a rectangular shape;
has an inclined inner edge so as to force the movement of the needle during the step of closing the jaws;
has a crenellated inner edge with a decreasing width between the end of the tooth and the base of the tooth;
has an enlarged upper end.
In the latter two cases, the variant improves the retention of the needle engaged in between the two jaws.

According to a particular variant, at least a portion of said teeth are elastically deformable, and has a curved end. In this case, these teeth are retractable and can be erased for the use of a needle with larger section or in case of particular positioning of the needle. According to one variant, the angle between the tooth and the surface of the jaw varies and/or the profile of the tooth varies.

According to an alternative embodiment, said teeth are formed by cutting the tubular casing of said jaws. In this case, the transverse surface consists of the edges of the cut shapes. According to a particular variant, said first jaw has a central channel of polygonal section which is complementary to the cross section of said mobile core. According to another variant, at least some of said teeth are axially movable. According to a particular embodiment, the end of said teeth has an oblique face in the tangential plane of the jaw.

Advantageously, each of the jaws has teeth with complementary oblique faces and in that the said second jaw is free to rotate with respect to the first jaw and comprises an elastic means with a torque aimed at bringing together the oblique faces of the complementary teeth. According to a particular variant, the needle holder has an end adapted to be connected to a motorized system.

BRIEF DESCRIPTION OF THE DRAWINGS

This invention will be better understood on reading the following description relating to several non-exhaustive samples of embodiments, with reference to the attached drawings where:

FIGS. 17 to 20 represent top views of different alternative embodiments of the implantation of the teeth;

FIGS. 21 to 26 show views along a radial sectional plane of various alternative embodiments of the teeth; and FIGS. 27 to 29 show views along a transverse sectional plane of various alternative embodiments of the teeth.

DETAILED DESCRIPTION

Description of a First Detailed Embodiment

Figure 1:
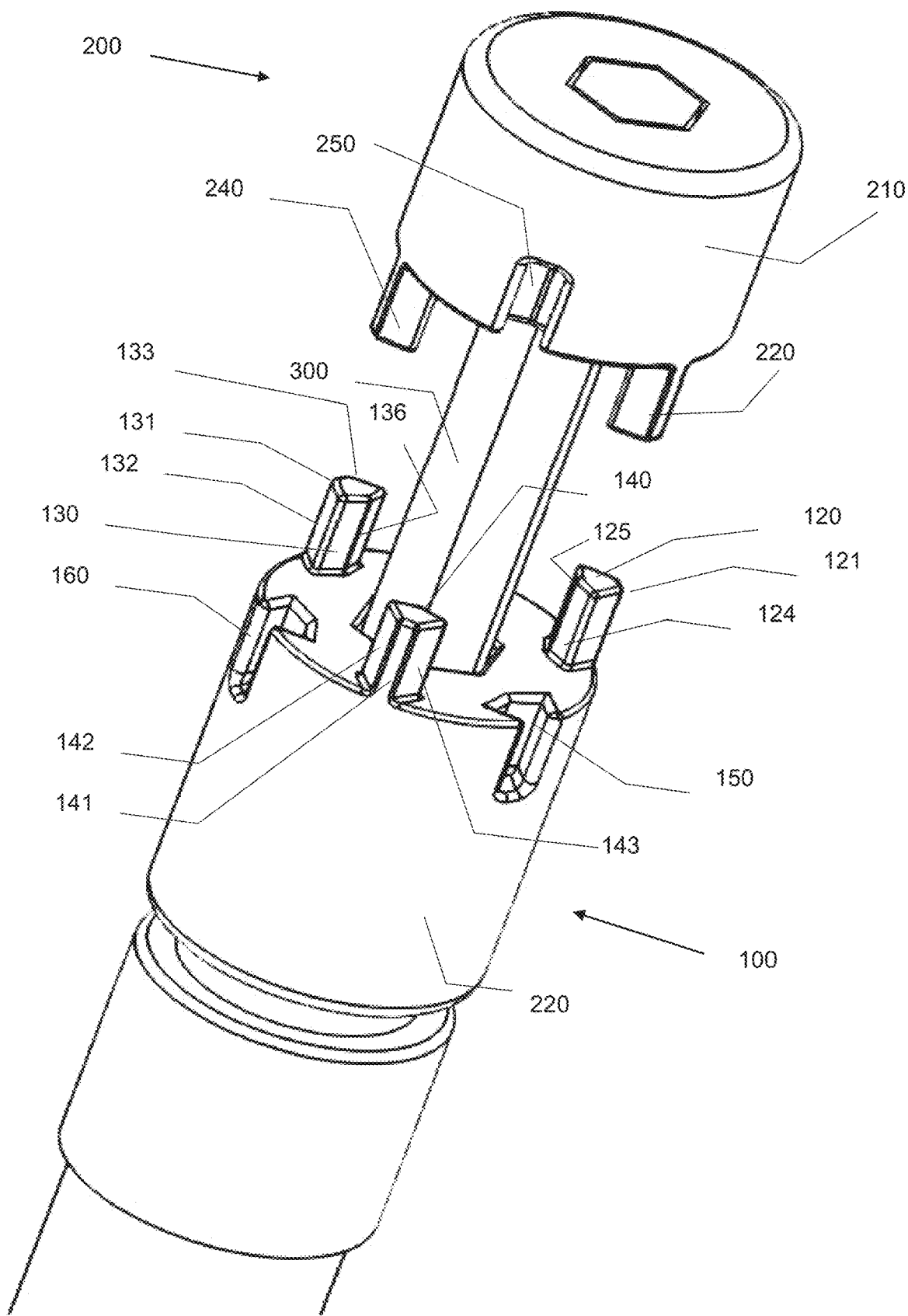
FIG. 1 represents a side view of the distal end of a first detailed embodiment of a needle holder according to the invention.
Figure 2:
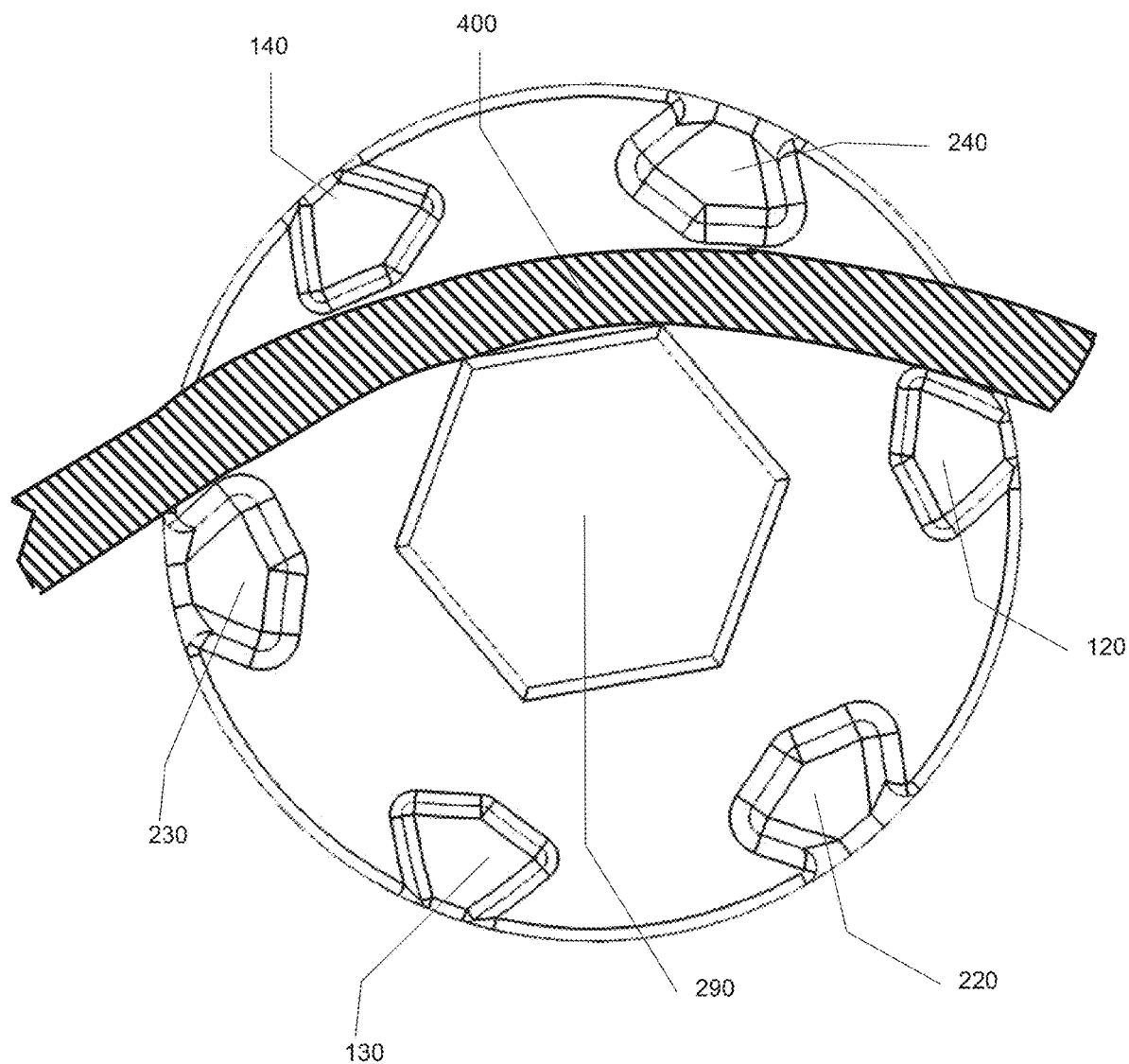
FIG. 2 represents a front view of the jaws carrying a curved needle according to this first detailed embodiment of a needle holder according to the invention.
Figure 3:
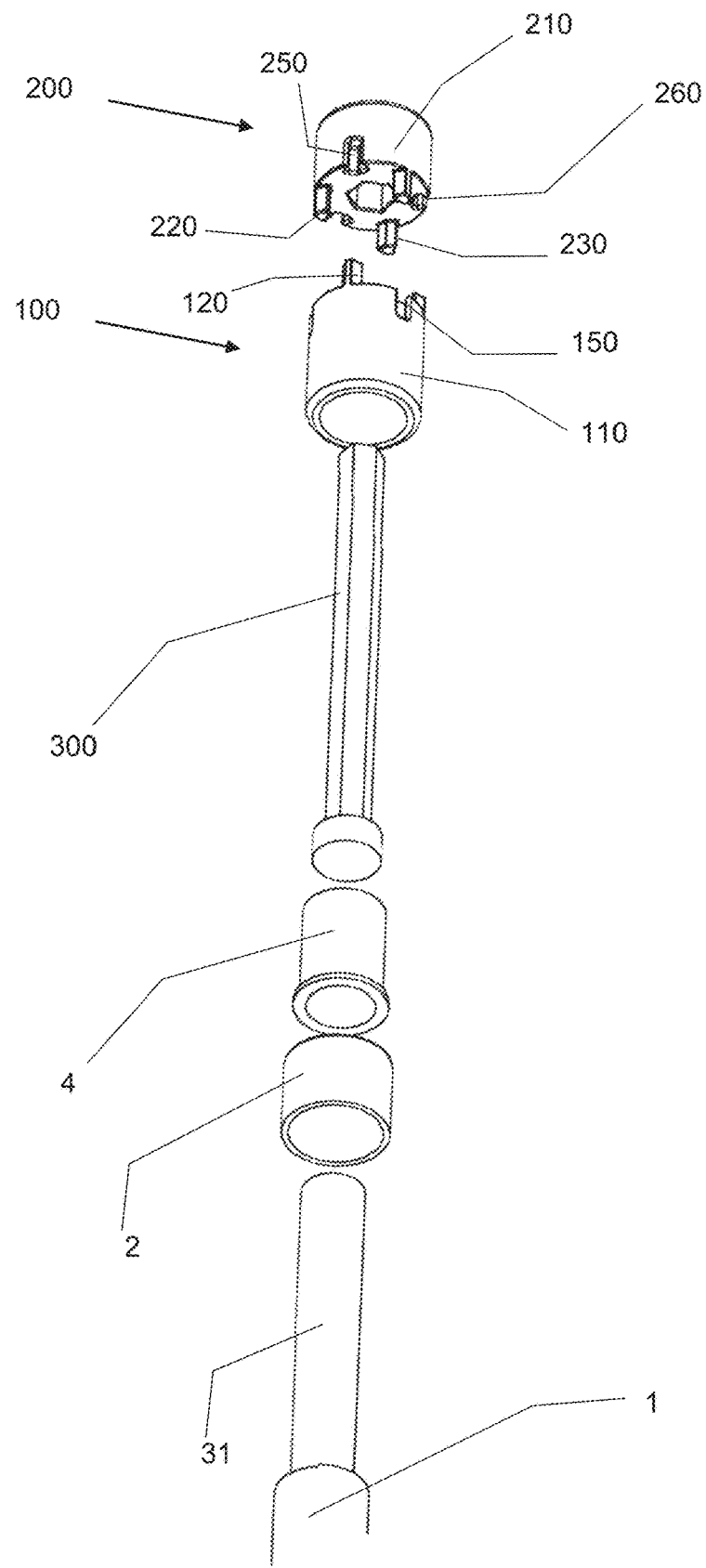
FIG. 3 represents an exploded overall view of this first detailed embodiment of a needle holder according to the invention.
Figure 4:
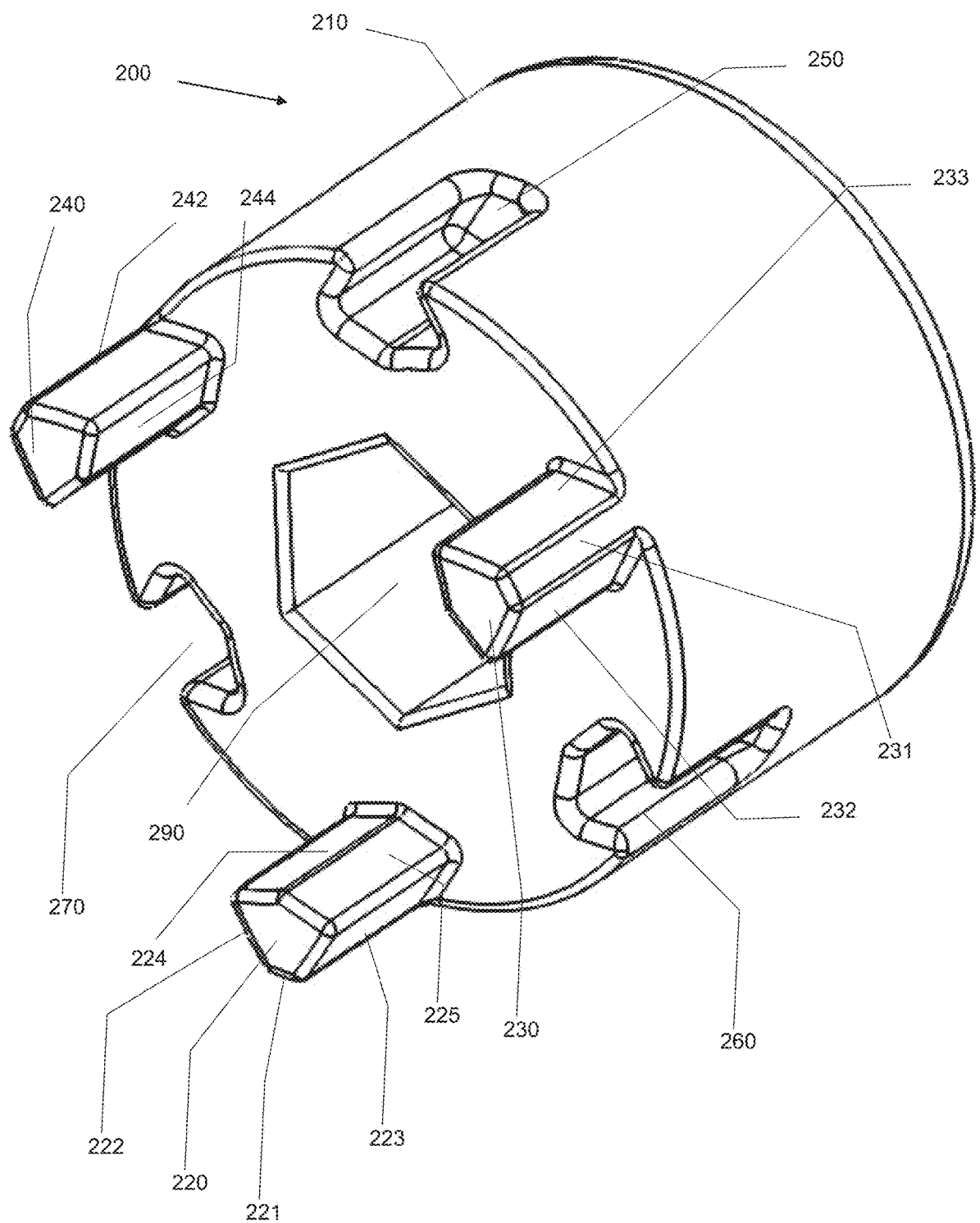
FIG. 4 represents a rear three-quarter perspective view of the second jaw of this first detailed embodiment of a needle holder according to the invention.
Figure 5:
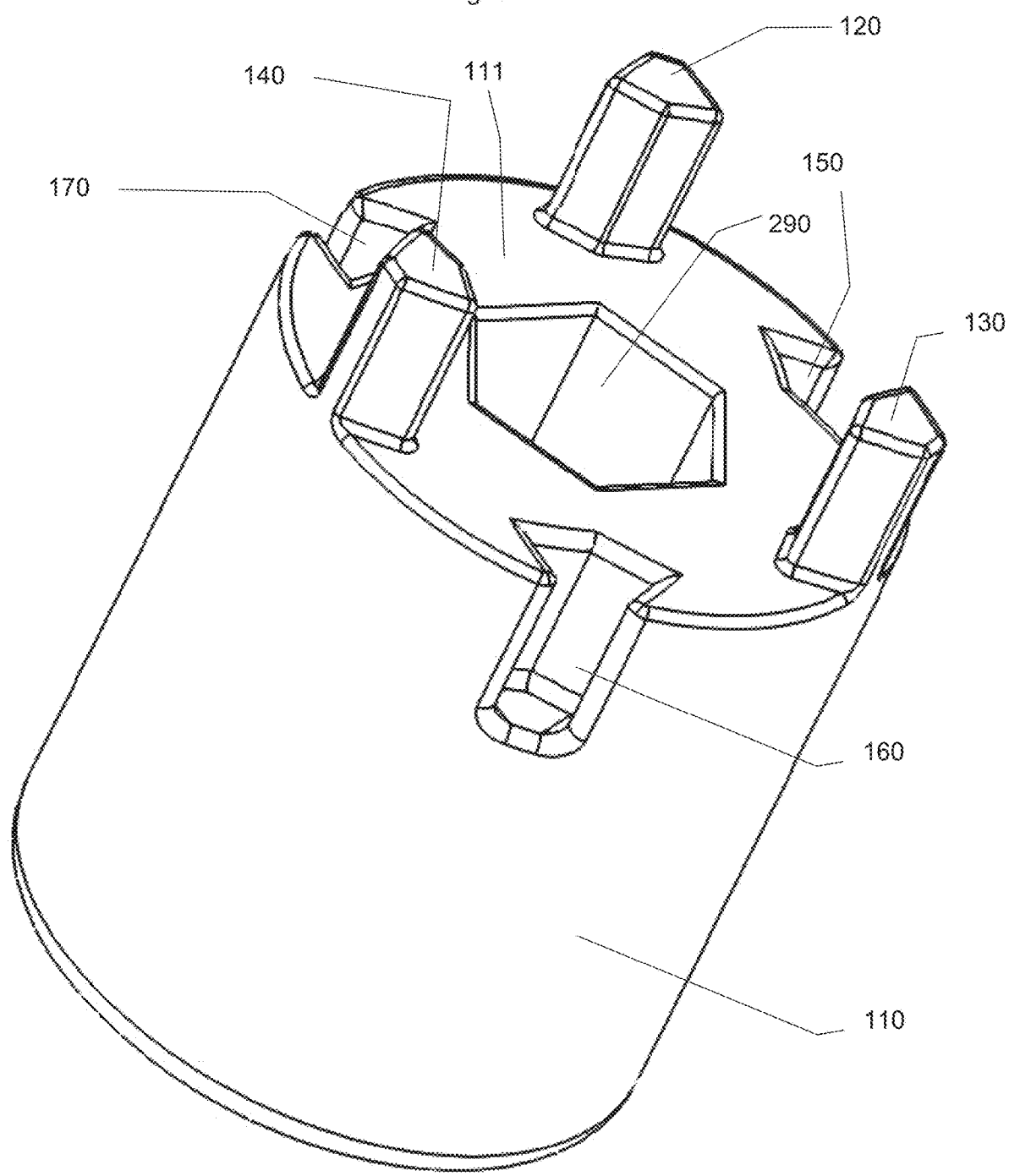
FIG. 5 represents a front three-quarter perspective view of the first jaw of this first detailed embodiment of a needle holder according to the invention.
Figure 6:
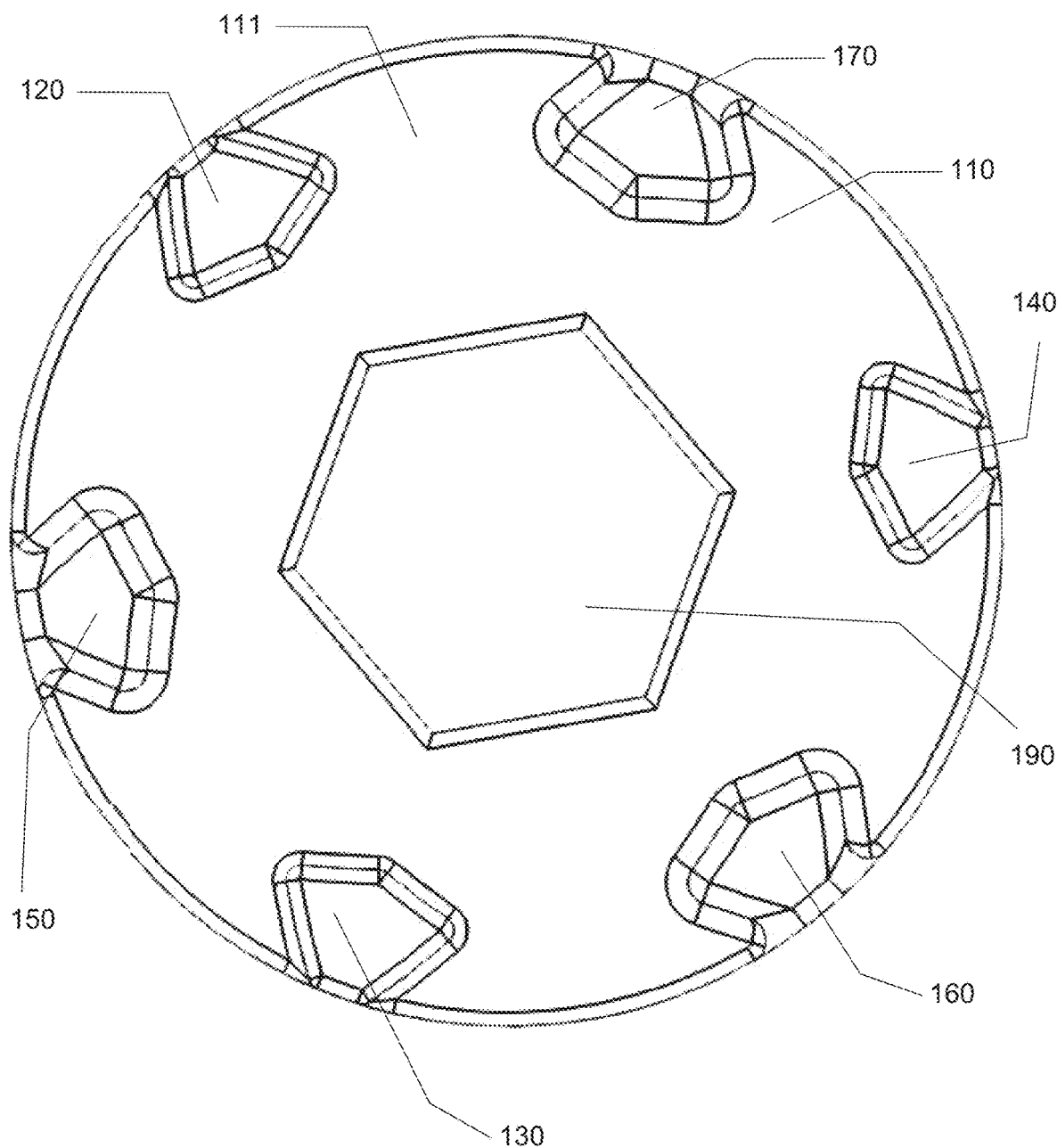
FIG. 6 represents a cross-sectional view of the first jaw of this first detailed embodiment of a needle holder according to the invention.
Figure 7:
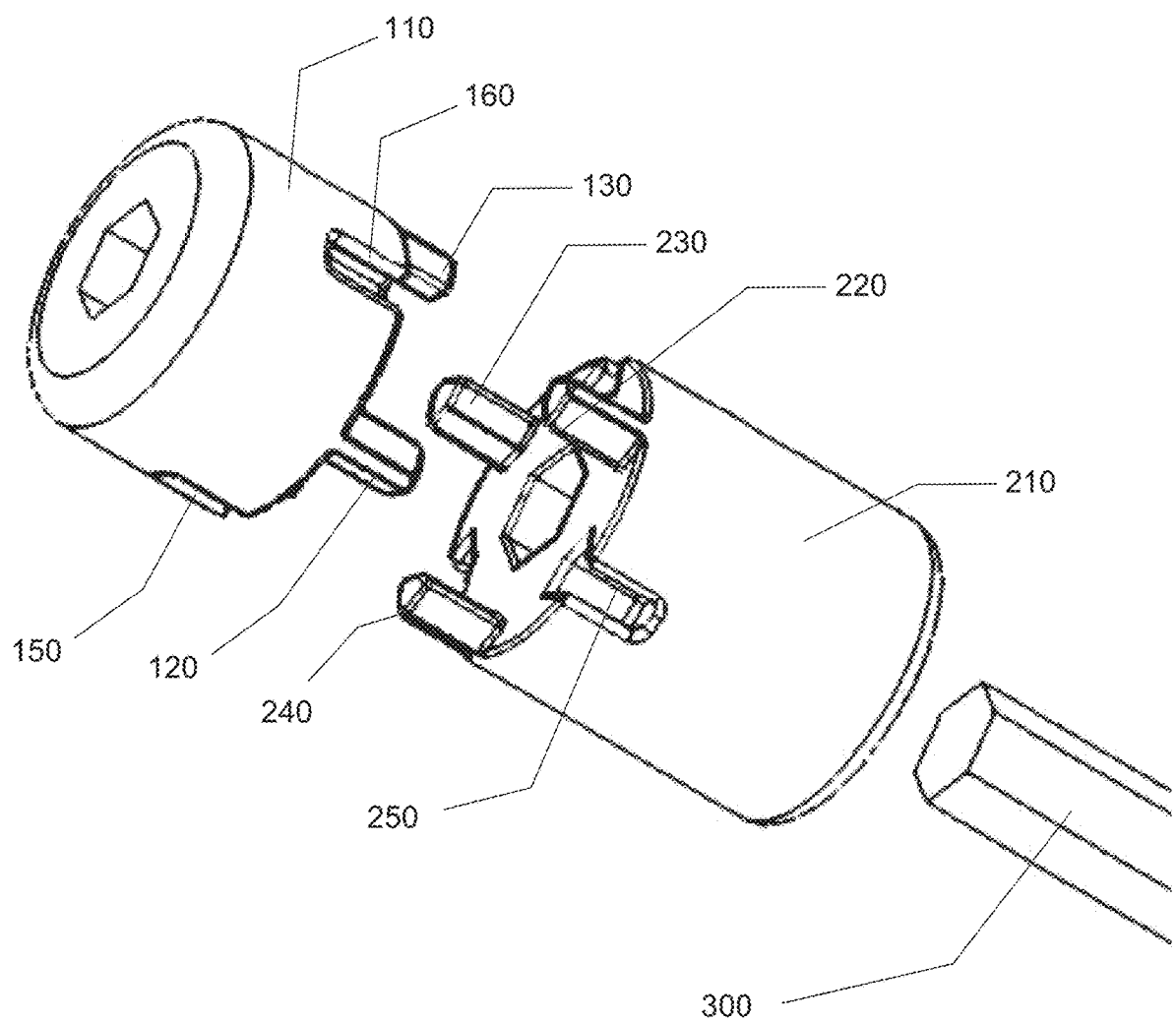
FIG. 7 represents a front three-quarter perspective view of the first jaw of this first detailed embodiment of a needle holder according to the invention.
Figure 8:
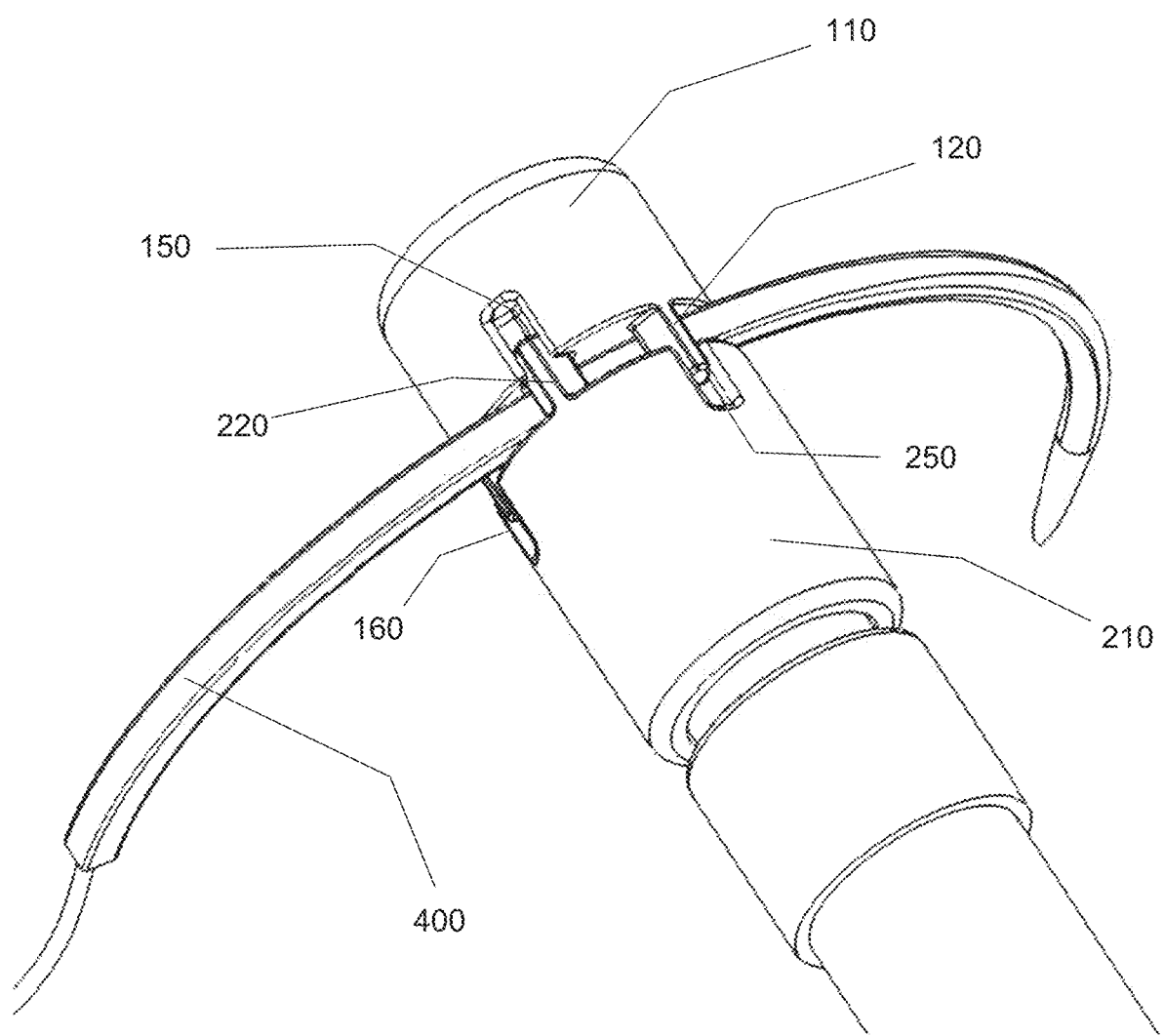
FIG. 8 represents a rear three-quarter perspective view of a needle holder according to the invention with a curved needle.
Figure 9:
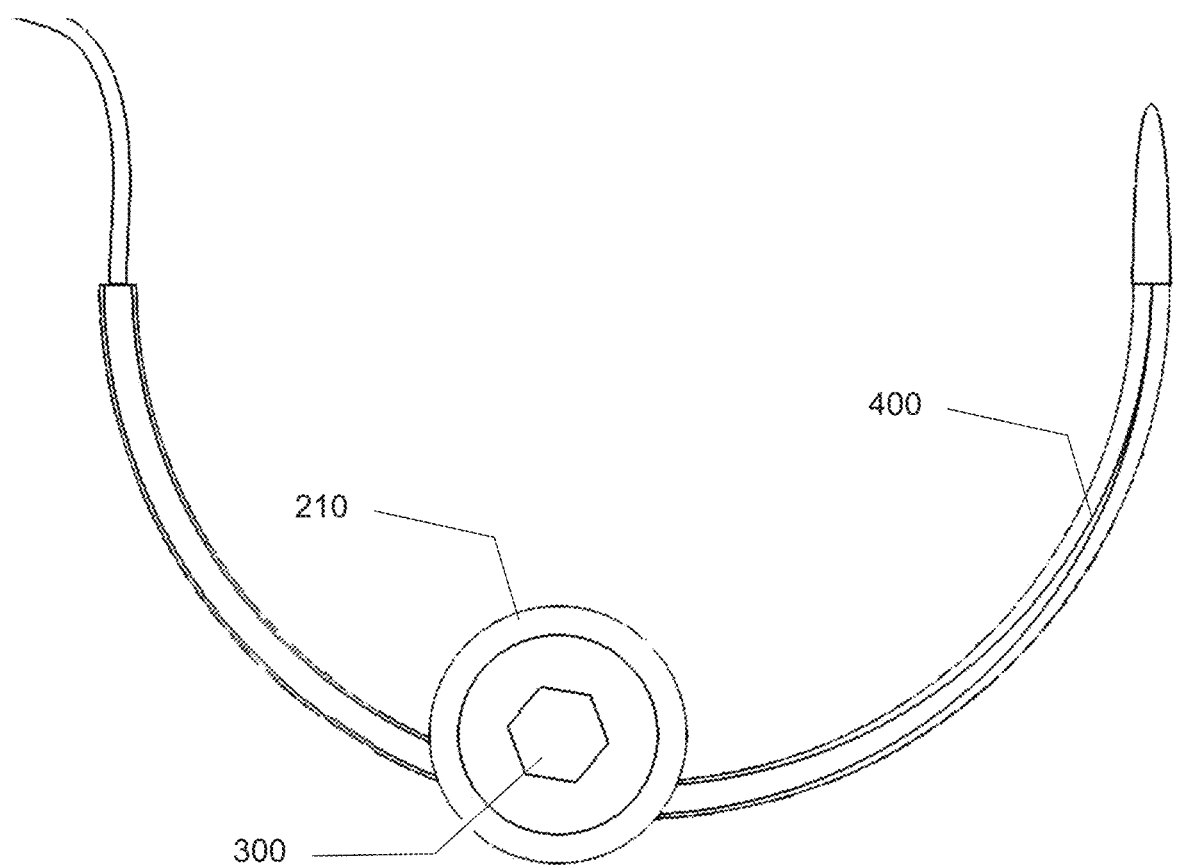
FIG. 9 represents a front view of a needle holder according to the invention with a curved needle.

The first detailed embodiment will be described in more detail with reference to FIGS. 1 to 9. The needle holder according to the first detailed embodiment consists of a first coaxial jaw (100) and a second coaxial jaw (200) with a stem (300). The first jaw (100) is mounted on a connecting ring (4) provided at the distal end of a stem (1) which is equipped with a connecting ring (2). The first jaw (100) has a cylindrical metal body (110) defining a flat front surface (111) directed towards the second jaw (200). This cylindrical body (110) is surmounted by three teeth (120, 130, 140) spaced angularly at 120° and arranged at the periphery of the front surface (111).

These teeth (120, 130, 140) have a pentagonal cross section, with:
- first semi-tubular sides (121, 131, 141) for extending the peripheral skirt of the cylindrical body (110);
- second and third sides (142, 143) forming an angle of between 30 and 70° with respect to the tangential plane to the cylindrical body (110), on either side of the radial plane;
- fourth and fifth sides (124, 125) connecting the edges of the second and third sides (122, 132, 143, 123, 133, 143) to a median edge, respectively (136).

These median edges (126, 136, 146) are located inside the second jaw, opposite the first sides (121, 131, 141). The radial plane passes through these central ridges (136) and a median line of the central ridges (136).

The second jaw (200) has a similar configuration, with three teeth (220, 230, 240) of the same shape as the teeth (120, 130, 140) of the first jaw (100), with a 60° offset to create an alternation between the fixed teeth and the moving teeth. It has a central lumen (290) of polygonal section which is complementary to the cross section of the stem (300).

The fixed body (110) and the movable body (210) next to each tooth of the opposite jaw grooves (150, 160, 170; 250, 260, 270) whose cross section is complementary to the cross section of an opposite jaw tooth and the depth adapted to allow the engagement of a tooth of the opposite jaw when the fixed (100) and movable (200) jaws are in a close position. The cylindrical body (110) of the jaw (100) is traversed by a channel (190) of hexagonal section which is complementary to the hexagonal section of the stem (300) to allow movement along the longitudinal axis of this stem (300). The body (210) of the second jaw (200) is fixed at the end of this stem (300). The angular orientation between the first jaw (100) and the second jaw (200) is fixed in this first detailed embodiment.

In an embodiment where each of the jaws has three teeth, a curved needle is housed between the consecutive teeth (230, 140, 240, 120) and the stem (300), and is pressed against the blanks of the teeth and the stem to ensure a stable positioning enabling the needle to be moved in a perfectly controlled manner. The teeth (220, 230, 240) have polygonal cross sections. In the example described, they each have five facets (221 to 225, 231 to 232, 242, 244).

The front end of the needle holder may include a pear-shaped handle, enabling such gestures as:
- displacement of the second jaw (200) in spacing or approximation with respect to the first jaw (100) by applying pressure on the handle;
- rotational displacement of the needle holder by a rotation of the handle;
- axial displacement of the needle holder by a linear movement of the handle.

The displacement of the needle holder is thus homothetic to the movements of the surgeon which leads to a very intuitive and precise manipulation. For a laparoscopic variant the handle will have a "gun" shape. For a robotics variant, the front end of the needle holder will not include a handle but will be coupled to a motorized system.

Description of a Second Detailed Embodiment

Figure 10:
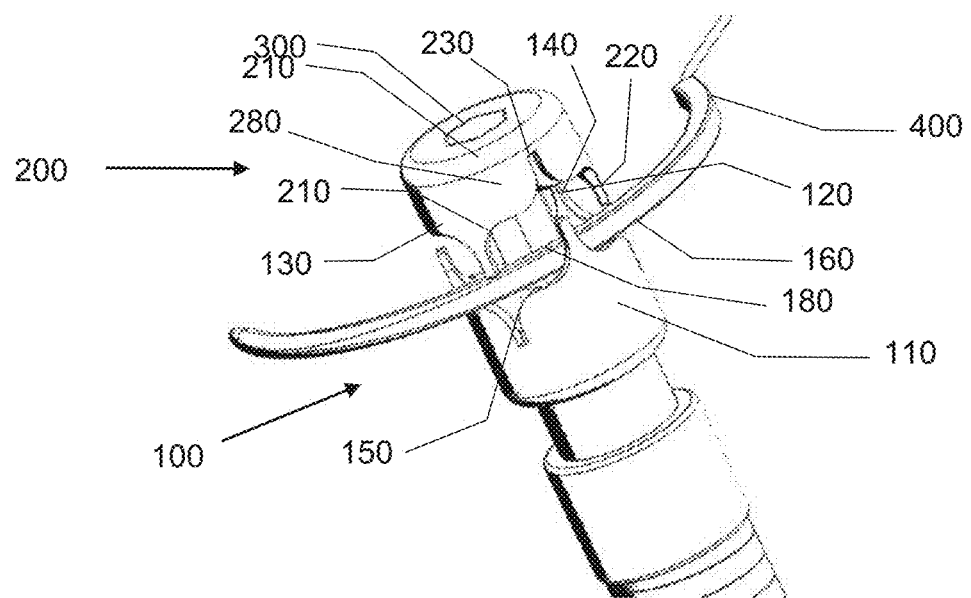
FIGS. 10 and 11 show perspective views of a second detailed embodiment with the jaws respectively in the open position and in the closed position.
Figure 11:
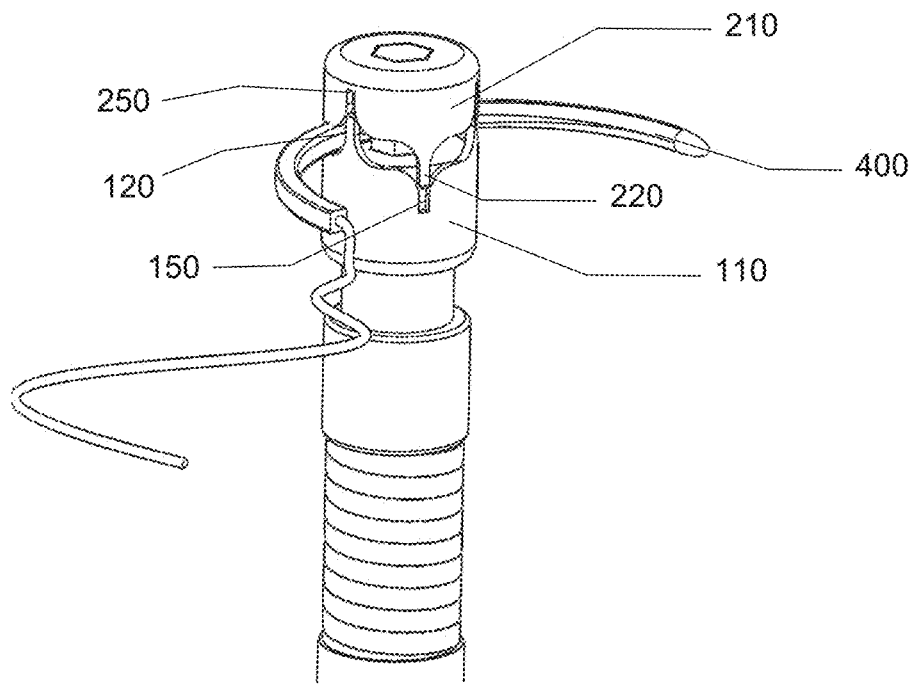

FIGS. 10 and 11 illustrate another embodiment where the two fixed (100) and movable (200) jaws maintaining the curved needle (400) are made by cutting a stamped sheet. The first jaw (100) has a tubular skirt (110) extended by flarings (120, 130) forming the teeth, and by cut-outs (150) into complementary shapes to the teeth (220, 230) of the second jaw (200). In the same way, the second jaw (200) has a tubular skirt (210) extended by flarings (220, 230) forming the teeth, and by cut-outs (250) into complementary shapes to the teeth (120, 130) of the first jaw (100). The connection zone between a tooth and a cut-out has a point of inflection with an edge (180, 280) defining the bearing surface of the needle (400), and fulfilling the function of the transverse surface of the jaw of the first detailed embodiment.

Description of a Third Detailed Embodiment

Figure 12:
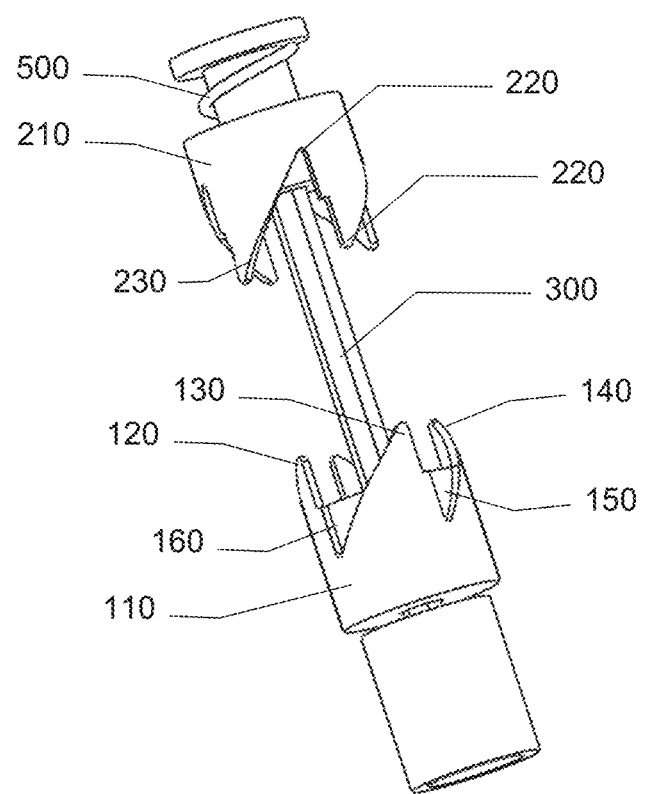
FIGS. 12 and 13 show perspective views of a third detailed embodiment with the jaws respectively in the open position and in the closed position.
Figure 13:
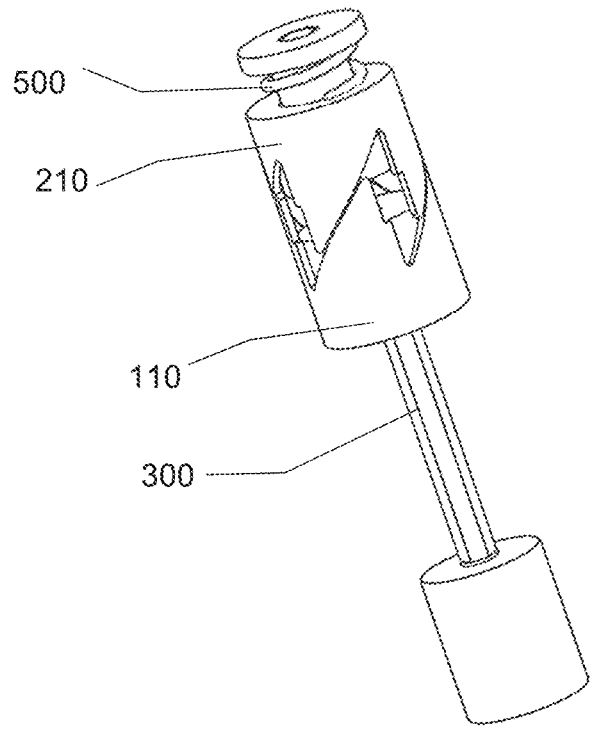

FIGS. 12 and 13 illustrate a detailed embodiment, the jaws each having four teeth cut in a tubular skirt (110, 210), with a section, in a tangential, triangular plane, with an alternation with four complementary shaped cuts to receive the teeth of the opposite jaw. The second jaw can rotate angularly around the core (300). A return spring (500) tends to bring the opposing teeth against each other.

In this variant, the teeth of the upper jaw have a different initial position compared to the previously described variants. They are secured to the second jaw (200) by the spring (500). When the jaw closes, it can turn while sliding against the opposite teeth until the needle is held between the edges of the skirt. As the pressure continues, the cylindrical portion of the jaw continues to descend until the needle is tightened both up and down. This configuration can accommodate a plurality of needles.

Description of a Fourth Detailed Embodiment

Figure 14:
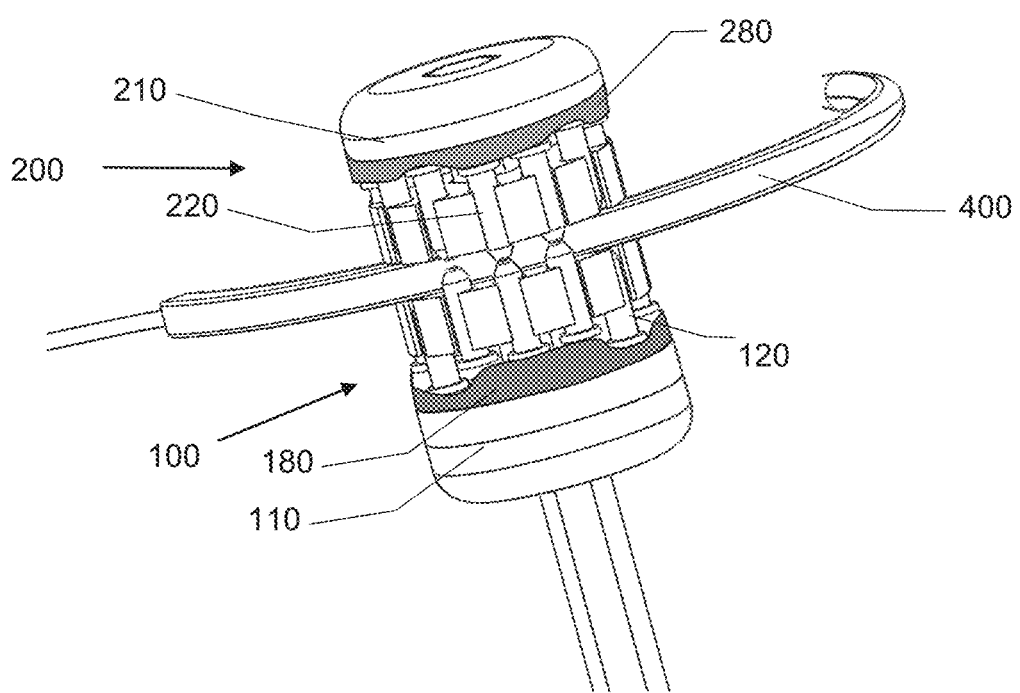
FIG. 14 represents a perspective view of a needle holder according to a fourth embodiment of the invention with a curved needle.

FIG. 14 shows a perspective view of a fourth detailed embodiment with the jaws in the closed position. The jaws (100, 200) have elastically deformable bearings (180, 280) on which the teeth (220, 120) rest.

In this variant, the teeth can slide in the jaws (100, 200) to accommodate a variety of needles. When the jaws close, some teeth come into contact with their pendants on the opposite jaw. Teeth that come in contact with the needle retract into the jaw. The bearings (180, 280) consisting of a flexible material (rubber, silicone, . . . ) provide a spring function to all the teeth so that they all come out when the jaws are open.

Description of a Fifth Detailed Embodiment

Figure 15:
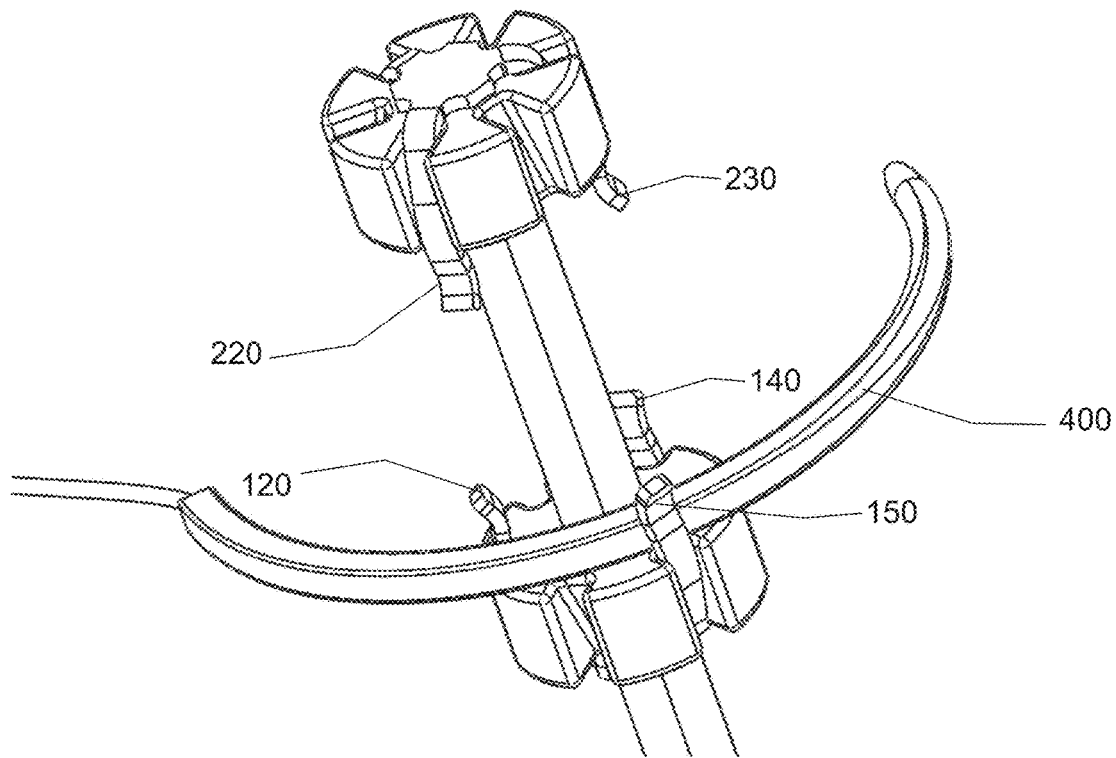
FIGS. 15 and 16 show perspective views of a fifth embodiment with the jaws respectively in the open position and in the closed position.
Figure 16:
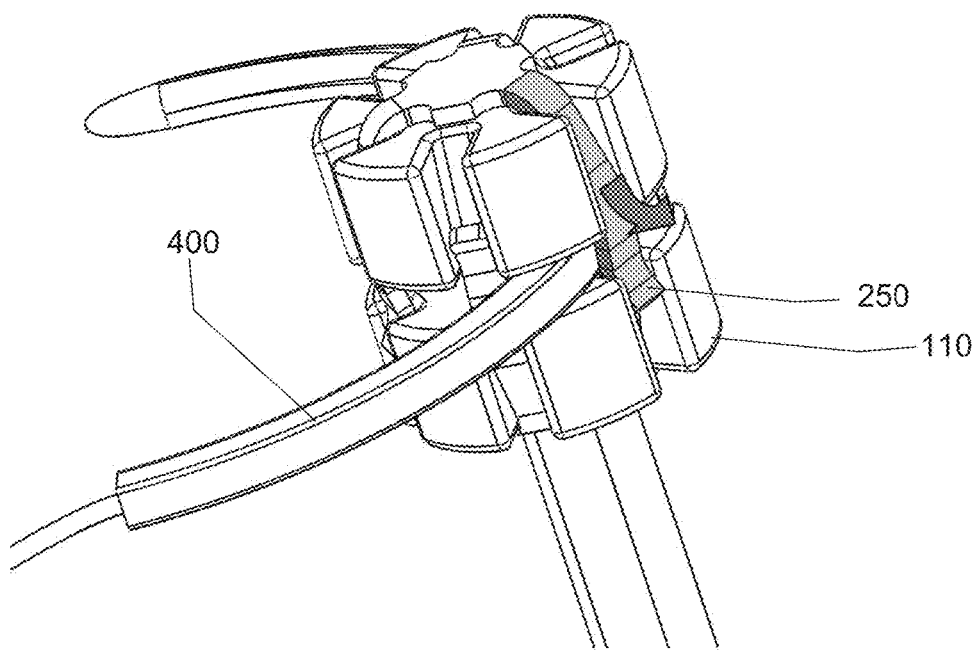

FIGS. 15 and 16 show perspective views of a fifth detailed embodiment with the jaws respectively in the open position and in the closed position. According to this variant, the teeth (120, 130, 140, 220, 230, 240) are flexible and come to push the needle (400) inwards due to the elasticity. In this variant, the teeth can undergo elastic deformation to adapt to a variety of needles. When the jaws close, some teeth move apart and position themselves on the outer circumference of the needle, while remaining channeled into the groove of the opposite jaw.

Implantation of the Teeth

FIGS. 17 to 20 represent top views of different alternative embodiments of the implantation of the teeth. The teeth can be arranged at the edge of the jaw as shown in FIG. 17. In this case, the outer edge of the teeth is in line with the body of the jaw without asperity or hollow.

They can also be set back from the edge of the jaw as shown in FIG. 18. In this case they reduce the lateral size.

They can also be arranged outside the jaw border, as shown in FIG. 19, to provide more attachment of a needle placed near the jaws. They can still be arranged straddling the edge of the jaw as shown in FIG. 20, for a compromise between improved attachment of the needle and a restricted lateral space.

Section of the Teeth

FIGS. 21 to 26 show views along a radial sectional plane of various alternative embodiments of the teeth. In the radial transverse plane the teeth may have a:
- rectangular section, with a flat or chamfered vertex, as shown in FIG. 21;
- rectangular section with a rounded top as shown in FIG. 22;
- rectangular section, with a flared top as shown in FIG. 23 to improve the retention of the needle;
- triangular section, as shown in FIG. 24 to bring the needle against the central core during the closure of the jaws;
- trapezoid section with increasing width towards the base of the tooth, with a curved inner edge as shown in FIG. 25, to ensure the guiding of the needle towards the centre during closure of the jaws;
- crenellated as shown in FIG. 26 to allow adaptation to different needle sizes.

Cross Section of the Teeth

FIGS. 27 to 29 show views along a transverse sectional plane of various alternative embodiments of the teeth. The section may be:
- circular as shown in FIG. 27;
- triangular with a rounded base as shown in FIG. 28, to present a central edge of support against the surface of the needle;
- pentagonal as shown in FIG. 29.

The invention claimed is:

1. An endoscopic needle holder for handling a curved needle, the endoscopic needle holder comprising: a remote actuator at one end of the needle holder; at another end, an articulated assembly comprising a first gripping jaw forming one piece with a duct and a second gripping jaw actuated by a mobile core in transverse displacement; the jaws including coaxial cylindrical parts with the mobile core; the first jaw including a plurality of longitudinally extending peripheral teeth; the second jaw including cylindrical parts with a plurality of peripheral teeth; and the second jaw being movable with respect to the first jaw by a longitudinal linear displacement between a rest position, where the jaws are spaced to delimit, between ends of the plurality of peripheral teeth, an interval at least equal to a section of the needle and a close position where they keep the needle curved; the plurality of peripheral teeth of the first jaw and the second jaw being laterally spaced apart from the mobile core and the duct; the jaws being configured to grasp and firmly hold the curved needle therebetween; a laterally flat surface located on the first jaw between the mobile core and the plurality of peripheral teeth, and between each adjacent pair of the plurality of peripheral teeth thereon; a laterally flat surface located on the second jaw between the mobile core and the plurality of peripheral teeth, and between each adjacent pair of the plurality of peripheral teeth thereon; and the flat surfaces facing each other.

2. The endoscopic needle holder according to claim 1 wherein the plurality of peripheral teeth of the second jaw are offset angularly with respect to the plurality of peripheral teeth of the first jaw.

3. The endoscopic needle holder according to claim 1 wherein the jaws have an alternation of peripheral teeth and peripheral grooves of complementary shapes and positions to the plurality of peripheral teeth of the opposite jaw.

4. The endoscopic needle holder according to claim 1 wherein the plurality of peripheral teeth of the first jaw and the second jaw have a polygonal cross section in a transverse plane.

5. The endoscopic needle holder according to claim 1 wherein the plurality of peripheral teeth of each of the jaws comprises three teeth and wherein each law has three grooves for receiving the three teeth of the complementary jaw.

6. The endoscopic needle holder according to claim 1 wherein an outer surface of the plurality of peripheral teeth of the first jaw and the second jaw are semi-cylindrical.

7. The endoscopic needle holder according to claim 1 wherein an outer diameter the plurality of peripheral teeth of one of the jaws is the same as an outer diameter of the other of the jaws, each of the plurality of peripheral teeth of the first jaw and the second jaw are longitudinally longer than wider at their distal ends, and the plurality of peripheral teeth of the first jaw and the second jaw are spaced apart from each other.

8. The endoscopic needle holder according to claim 1 wherein an outer diameter of the plurality of peripheral teeth of one of the jaws is smaller than an outer diameter of the other of the jaws, each of the plurality of peripheral teeth of the first jaw and the second jaw are longitudinally longer than wider at their distal ends, and the plurality of peripheral teeth of the first jaw and the second jaw are spaced apart from each other.

9. The endoscopic needle holder according to claim 1 wherein an outer diameter of the plurality of peripheral teeth of one of the jaws is greater than an outer diameter of the other of the jaws, each of the plurality of peripheral teeth of the first jaw and the second jaw are longitudinally longer than wider at their distal ends, and the plurality of peripheral teeth of the first jaw and the second jaw are spaced apart from each other.

10. The endoscopic needle holder according to claim 1 wherein the second jaw has a hemispherical end.

11. The endoscopic needle holder according to claim 1 wherein a section of the plurality of peripheral teeth of the first jaw and the second jaw, in a radial plane, is rectangular.

12. The endoscopic needle holder according to claim 1 wherein a section of the plurality of peripheral teeth of the first jaw and the second jaw, in a radial plane, has an inclined inner edge.

13. The endoscopic needle holder according to claim 1 wherein a section of the plurality of peripheral teeth of the first jaw and the second jaw, in a radial plane, has a crenellated inner edge with a decreasing width between an end of the tooth and a base of the tooth.

14. The endoscopic needle holder according to claim 1 wherein a section of the plurality of peripheral teeth of the first jaw and the second jaw, in a radial plane, has an enlarged upper end.

15. The endoscopic needle holder according to claim 1 wherein at least a portion of the plurality of peripheral teeth of the first jaw and the second jaw are elastically deformable, and has a flared end.

16. The endoscopic needle holder according to claim 1 wherein the first jaw includes a central channel having a polygonal cross sectional shape which is complementary to a cross section of the movable core.

17. The endoscopic needle holder according to claim 1 wherein at least some of the plurality of peripheral teeth of the first jaw and the second jaw are axially movable.

18. The endoscopic needle holder according to claim 1 wherein an end of each of the plurality of peripheral teeth of the first jaw and the second jaw has an oblique face in a tangential plane of the jaws.

19. The endoscopic needle holder according to claim 18 wherein each of the plurality of peripheral teeth of the first jaw and the second jaw has teeth with complementary oblique faces, and the second jaw is free to rotate with respect to the first jaw and comprises an elastic means with a torque aimed at bringing together oblique faces of the complementary teeth.

20. The endoscopic needle holder according to claim 1 further comprising an end adapted to be connected to a motorized system.

21. The endoscopic needle holder of claim 1 further comprising grooves located in each of the jaws between the plurality of peripheral teeth projecting therefrom to allow the plurality of peripheral teeth of the other of the jaws to being received within the grooves when the jaws firmly grip the curved needle, and the grooves and the plurality of peripheral teeth of the first and second jaw being laterally spaced away from the stem.

22. An endoscopic needle holder comprising: a curved endoscopic suturing needle; an actuator at one end of the needle holder; another end of the needle holder comprising a first gripping jaw and a second gripping jaw, each of the jaws including a polygonal hole; a longitudinally elongated stem having a polygonal cross-sectional shape, extending through the holes of the jaws; the first jaw including a plurality of longitudinally extending and peripherally spaced apart teeth; the second jaw including a plurality of longitudinally extending and peripherally spaced apart teeth; the second jaw being movable with respect to the first jaw by a longitudinal linear displacement between an open and spaced apart position, and a closed position where the curved needle is gripped between the jaws with the curved needle being laterally elongated between at least some of the plurality of teeth of the first and second jaw and the stem while projecting laterally past a periphery of the jaws; the plurality of teeth of the first jaw and the second jaw being laterally spaced away from the stem; grooves located in each of the jaws between the plurality of teeth projecting therefrom to allow the plurality of teeth of the other of the jaws to be received within the grooves when the jaws firmly grip the curved needle; and the grooves and the plurality of teeth of the first and second jaw being laterally spaced away from the stem.

23. An endoscopic needle holder comprising: a cylindrical first gripping jaw and a cylindrical second gripping jaw, each of the jaws including a co-axial central hole; a longitudinally elongated stem extending through the holes of the jaws; the first jaw including at least three spaced apart teeth; the second jaw including at least three spaced apart teeth, the teeth of the first jaw projecting toward the second jaw, and the teeth of the second jaw projecting toward the first jaw; the second jaw being longitudinally and endoscopically movable with respect to the first jaw; the jaws being configured to grip a curved needle therebetween with a pointed end of the curved needle laterally projecting laterally external to the jaws; the teeth of the first jaw and the second jaw being laterally spaced away from the holes; a laterally flat surface of the first jaw located between the central hole thereof and the teeth projecting from the first jaw; a laterally flat surface of the second jaw located between the central hole thereof and the teeth projecting from the second jaw; grooves located in each of the jaws between the teeth projecting therefrom to allow the teeth of the other of the jaws to being received within the grooves when the jaws firmly grip the curved needle; and the flat surfaces contacting against each other when the teeth of the first and second jaw are fully received in the grooves.

24. The endoscopic needle holder of claim 23, wherein the teeth of the first and second jaw have a polygonal cross section in a transverse plane.

25. The endoscopic needle holder of claim 23, wherein an outer surface of the teeth of the first and second jaw is semi-cylindrical.

26. An endoscopic needle holder for handling a curved needle, the endoscopic needle holder comprising: a remote actuator at one end of the needle holder; at another end, an articulated assembly comprising a first gripping jaw forming one piece with a duct and a second gripping jaw actuated by a mobile core in transverse displacement; the jaws including coaxial cylindrical parts with the mobile core; the first jaw including a plurality of longitudinally extending peripheral teeth; the second jaw including cylindrical parts with a plurality of peripheral teeth; and the second jaw being movable with respect to the first jaw by a longitudinal linear displacement between a rest position, where the jaws are spaced to delimit, between ends of the plurality of peripheral teeth of the first and second jaw, an interval at least equal to a section of the needle and a close position where they keep the needle curved; the plurality of peripheral teeth of the first and second jaw being laterally spaced apart from the mobile core and the duct; the jaws being configured to grasp and firmly hold the curved needle therebetween; grooves located in each of the jaws between the plurality of peripheral teeth projecting therefrom to allow the plurality of peripheral teeth of the other of the jaws to be received within the grooves when the jaws firmly grip the curved needle, and the grooves and the plurality of peripheral teeth of the first and second law being laterally spaced away from the core.

27. The endoscopic needle holder according to claim 26 wherein the plurality of peripheral teeth of the first jaw and the second jaw extend from a tubular casing of the jaws.

* * * * *